Feb. 13, 1968 H. A. JOHNSON, JR ET AL Plant Pat. 2,796
STRAWBERRY PLANT
Filed Feb. 23, 1966
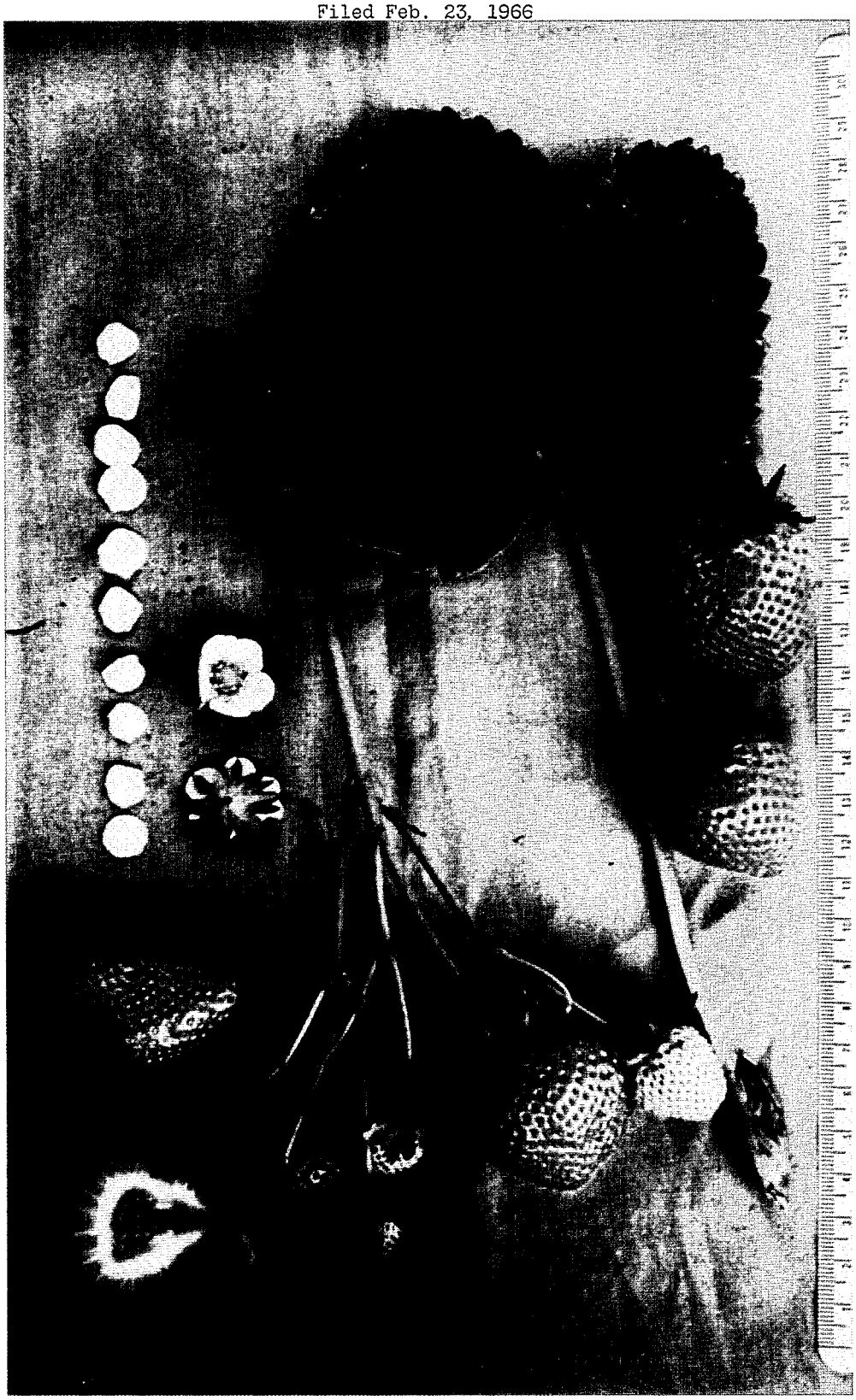
INVENTORS
HAROLD A. JOHNSON, JR.
HAROLD E. THOMAS
BY TOWNSEND & TOWNSEND
ATTORNEYS United States Patent Office Plant Pat. 2,796
Patented Feb. 13, 1968

2,796
STRAWBERRY PLANT

Harold A. Johnson, Jr., and Harold E. Thomas, Morgan Hill, Calif., assignors, by mesne assignments, to Driscoll Strawberry Associates, Inc., Gilroy, Calif., a corporation of California Filed Feb. 23, 1966, Ser. No. 529,621
1 Claim. (Cl. Plt.—49)

This invention relates to a new and distinct variety of strawberry plant which is the result of a cross of the unpatented spring producing variety known as The Strawberry Institute of California selection No. C72.26 and the subject of United States Plant Patent No. 1,735 to Goldsmith issued July 29, 1958. The C72.26 selection is derived from a cross of the University of California varieties known as Cal. 677.10 and Cal. 752.46.

The seedlings resulting from the aforementioned cross were grown and asexually multiplied in Tehama County, Calif.; and tested in the fruiting beds of The Strawberry Institute's selection and testing grounds at San Martin, Calif. Clones of these seedlings were also held at The Strawberry Institute's Propagation Nursery in Shasta County. One plant was selected from the aforementioned group of seedlings, and further asexual reproduction was performed in the Shasta County nursery of the institute. Tests followed in various parts of California during intervening seasons on various institute members' properties. These tests indicated the merit of this new plant and resulted in its selection as a promising test variety.

A plant of the new variety typical in size, shape and color is pictured in the accompanying drawing in which five ripe berries are shown, indicating some of the variations in shape found in this variety. Also, a sixth berry is shown in cross section to exemplify flesh color and core cavity. The inflorescence pictured is typical of branching and relative size on and about the early part of August, during which period the leaf is also typical in appearance and size. The flower, petals, and calyx shown are from secondary flowers.

A distinguishing characteristic of this new plant is than when planted in southern California during the summer, and cropped the following spring, the plant is slightly smaller and more open than the variety Lassen which was introduced by the University of California College of Agriculture in 1945 and is known to the Bureau of Plant Industry Agricultural Research Center at Beltsville, Md. Also, the plant of the present invention changes morphologically as the season progresses, regardless of which fruiting area in California it is grown. This new variety is smaller, darker and more prostrate in early spring, but the petioles and leaflets become longer, larger, more erect, and lighter in color as the season progresses from spring to fall. The early spring growth in the central coast area is not as prostrate as it is in southern California. Moreover, the plant will produce a large multiple crown during the fruiting year and, if held for a second year, will become dense. The leaflets are darker, more rugose, and the margin serrations are not as deep or as pointed at the apex as Lassen. The plant is a good runner maker in the nursery, with normally a higher increase rate than Lassen.

Another group of characteristics distinguishing this new variety is in the various features of its fruit. For example, the berries of this invention are usually larger, firmer, and have a smoother surface than the fruit of Lassen. The primary berries are generally of an irregular wedge shape, with the first primaries in the spring having distinct longitudinal furrows. Subsequent primaries lack the furrows but, when viewed from the side, are often conic in outline and appear three-sided from the apical end. This is in contrast to primary berries of most other varieties which generally have a greater width than length even when compared to the Lassen variety normally having a greater length than width. The secondary and tertiary berries of the new variety are usually globose conic to conic in shape. The surface color is generally more uniform than the Lassen variety; this is especially true in the spring. Moreover, this invention generally has smaller seeds held in a less sunken position in relation to the fruit surface than does the Lassen variety. The flesh surface color is not consistently red, and some areas become pink to almost white as does Lassen.

A further characteristic distinguishing this new variety is that the first primary berries in the spring crop are borne on single fruit stalks which originate from the crown. Such single fruit stalks or pedicels are relatively short compared to later inflorescences. As the season progresses a secondary berry plus the primary berry is formed and the inflorescence now includes a peduncle plus two pedicels. Subsequent inflorescences may produce two or more secondary berries plus tertiary berries which originate from fruit stalks that have branched to the second and third order. Lassen produces some primaries with single pedicels originating from the crown, but not as abundantly as the new variety. During the late spring and summer crop with the new variety, most pedicels holding primary berries originate from the side of a peduncle near the axil formed by the union of the peduncles, while relatively few pedicels bearing primary berries originate from the axil. This is in contrast to Lassen where such pedicels holding primary berries usually occur at the axil. The fruit-bearing stalks of this invention are generally larger in diameter than Lassen.

The calyx of this new variety is larger and the serrations on the sepals are more abundant than in the Lassen. The sepals generally overlap each other at the point where they join the pedicel; the smaller sepals overlap the larger and are farthest from the fruit surface.

In comparison to the Lassen variety, the dessert quality of this variety is superior, with a mild sub-acid flavor. There is generally no particular aroma peculiar to the flesh of this new variety.

When planted during the summer, and grown with plastic mulch, the fruiting season in southern California for this variety is normally about the same as that for Lassen; a small production occurs during March with the main peak during April and another the last of June or early July. This same cycle of production occurs in the central coast area, but its occurrence is at least a month later. Production will continue into the fall in both areas, but the fruit remains firm even though it becomes smaller. If planted during the winter, this variety will not continue in production the first year during the late spring and summer, as will Lassen.

The new variety of this invention has a relatively high level of Verticillium wilt resistance, but is susceptible to the red stele disease. As a seedling this variety withstood the natural virus invasion of the virus components found in the Santa Clara Valley without losing its ability to produce, but it has not been tested for its resistance against virus since that time. The invention is suceptible to powdery mildew, especially during the first growing year, and also to two spotted mite.

The varietal characteristics of this new plant described below in detail were observed during the first fruiting year following summer planting. Observations were made in the Oxnard, Santa Maria, Salinas and Watsonville areas of California which are cool coastal areas near the Pacific Ocean. The color terminology is in accordance with Ridgways Color Standards and Nomenclature (1912 edition).

*Plant.*—Medium to large size, open to medium dense, and extensive root system.

*Leaves.*—Medium to large size. The central leaflet diameter is 5 to 8.5 cm. with the length usually greater than width. Petioles and leaflets become lighter in color, longer and more erect as the season progresses. Leaflets are moderately rugose. Bracts may or may not be present on petioles. Serrations on leaflet margins are ovate with an acute apex. The leaflet upper side color in Oxnard during April is Dark Cress Green, Plate XXXI; and in the central coast area during August is Parrot Green, Plate VI.

*Runners.*—Vigorous; medium to long internodes. Many runners are produced in the fruiting beds after summer planting. Nursery production of plants is high.

*Inflorescences.*—Short, 10 to 20 cm., during the first spring crop, becoming long, 20 to 26 cm., as the season progresses. During the first spring crop, most fruit is produced on single fruiting stalks originating from the crown; as the season progresses, most pedicels holding primary berries originate from the side of a peduncle near the axil formed by the branching of the main fruiting stalk (see drawing photograph). Two or three peduncles may originate from such axil. Some of the pedicels holding the primary berries originate from the axil and not from a peduncle. Most hair on the tertiary pedicel 20 mm. below the flower usually lays against and parallel to the pedicel, but at times some hair forms an angle of 45 degrees with the pedicel. Flowers may be visible above the foliage.

*Fruit.*—Large; dropping in size during the season. Primary berries in the spring grow to an average of 40 mm. in length and 45 mm. in width. First primaries in spring are of irregular wedge to conic in form, often with longitudinal furrows giving irregular appearance.

Subsequent primaries are not as rough; often conic in outline when viewed from the side and three-sided in outline from the apical end. Secondary and tertiary berries are generally globose conic to conic as described in the U.S.D.A. Bulletin 1043. The shoulders of most berries are large and round, not necked. The fruit surface is smooth and firm with high gloss. Surface color is Carmine, Plate I. The flesh is firm and juicy having a perimeter color of Scarlet Red, Plate I; and a center of core color of Peach Red, Plate I.

*Seeds.*—Abundant and evenly spaced, very few nonfertile, small to medium size. The seeds may be held slightly below to above the fruit surface. Seed color is Apricot Yellow, Plate IV, becoming dark when exposed to full sunlight.

*Calyx.*—Large; the calyx of most primary berries is 35 to 45 mm. in diameter and usually joins the pedicel at a point below the fruit outline if the berry is viewed from the side, often giving the calyx an irregular reflexed shape rather than a symmetrical outline. The sepals are large and serrated on the primary berries, but the serrations are scarce on secondaries and tertiaries. The calyx is usually free of the surface of the fruit, which is capped with difficulty except when fully ripe. The color of the sepal on the side facing the fruit is Ivy Green, Plate XXXI.

We claim:

1. The new and distinct variety of strawberry plant herein described and illustrated, and identified by the characteristics enumerated above.

No references cited.

ROBERT E. BAGWILL, *Primary Examiner.*